(12) United States Patent
De Silva et al.

(10) Patent No.: US 7,387,123 B2
(45) Date of Patent: Jun. 17, 2008

(54) GAS IDENTIFICATION SYSTEM AND VOLUMETRICALLY CORRECT GAS DELIVERY SYSTEM

(75) Inventors: Adrian D De Silva, Riverside, CA (US); Samuel A Glukhov, Sherman Oaks, CA (US)

(73) Assignee: VIASYS Manufacturing, Inc., Yorba Linda, CA (US)

( * ) Notice: Subject to any disclaimer, the term of this patent is extended or adjusted under 35 U.S.C. 154(b) by 1380 days.

(21) Appl. No.: 09/998,084

(22) Filed: Nov. 30, 2001

(65) Prior Publication Data

US 2003/0106554 A1   Jun. 12, 2003

(51) Int. Cl.
A61M 16/00 (2006.01)
A62B 7/00 (2006.01)

(52) U.S. Cl. .......................... 128/204.22; 128/204.18; 128/205.11

(58) Field of Classification Search ...... 128/203.12–14, 128/203.25, 204.18, 204.21, 205.11, 205.14, 128/204.22, 204.23, 204.29, 205.15, 205.18, 128/205.2, 205.23
See application file for complete search history.

(56) References Cited

U.S. PATENT DOCUMENTS

| | | | |
|---|---|---|---|
| 3,722,510 A | 3/1973 | Parker | |
| 3,831,594 A | 8/1974 | Rein | |
| 3,859,995 A | 1/1975 | Colston | |
| 3,916,889 A | 11/1975 | Russell | |
| 4,014,384 A | 3/1977 | Marcus | |
| 4,072,148 A | 2/1978 | Munson et al. | |
| 4,085,766 A | 4/1978 | Weigl et al. | |
| 4,182,324 A | 1/1980 | Hills | |
| 4,190,045 A | 2/1980 | Bartels | |
| 4,195,949 A | 4/1980 | Reiher | |
| 4,271,701 A | 6/1981 | Dempster et al. | |
| 4,442,835 A | 4/1984 | Carnegie | |
| 4,602,653 A | 7/1986 | Ruiz-Vela et al. | |
| 4,776,332 A | 10/1988 | Wenzel et al. | |
| 4,821,732 A | 4/1989 | Lippes | |
| 4,883,051 A | 11/1989 | Westenskow et al. | |
| 4,939,647 A | 7/1990 | Clough et al. | |
| 4,964,404 A * | 10/1990 | Stone | 128/204.22 |
| 4,974,585 A | 12/1990 | Stone | |
| 4,989,456 A | 2/1991 | Stupecky | |
| 4,993,269 A | 2/1991 | Guillaume et al. | |
| 5,069,220 A | 12/1991 | Casparie et al. | |
| 5,159,924 A * | 11/1992 | Cegielski et al. | 128/203.12 |
| 5,197,895 A | 3/1993 | Stupecky | |
| 5,263,369 A | 11/1993 | Cutler | |
| 5,405,269 A | 4/1995 | Stupecky | |
| 5,429,123 A * | 7/1995 | Shaffer et al. | 128/204.23 |

(Continued)

Primary Examiner—Teena Mitchell
(74) Attorney, Agent, or Firm—Baker & Hostetler LLP (57) ABSTRACT

A gas delivery system, having a gas identification, by which a gas supplied to the gas delivery system is identified, a blender, blending oxygen and the gas to provide a gas mixture with an oxygen flow rate set up by an operator, and at least one flow sensor, to measure a flow rate of the gas mixture. The blender is driven by an actuator motor to various blender positions with the blender positions being calibrated based on the specific heat ratio and the gas constant of the gas. The flow sensor can be installed at the inspiratory circuit, the proximal circuit and the expiratory circuit of the gas delivery system. The flow sensor output is corrected based on the actual conditions, including the temperature, pressure and humidity, and characteristics of the gas mixture.

7 Claims, 4 Drawing Sheets

U.S. PATENT DOCUMENTS

| | | | |
|---|---|---|---|
| 5,460,039 A * | 10/1995 | Cutler | 73/204.15 |
| 5,503,145 A * | 4/1996 | Clough | 128/204.22 |
| 5,558,083 A * | 9/1996 | Bathe et al. | 128/203.12 |
| 5,678,542 A * | 10/1997 | Maffatone | 128/205.24 |
| 5,699,790 A * | 12/1997 | Bathe et al. | 128/204.22 |
| 5,727,545 A * | 3/1998 | Psaros | 128/203.12 |
| 5,730,119 A * | 3/1998 | Lekholm | 128/200.24 |
| 5,794,616 A * | 8/1998 | Cochran et al. | 128/205.11 |
| 5,837,904 A | 11/1998 | Porter | |
| 5,848,591 A * | 12/1998 | Weismann | 128/204.22 |
| 5,887,611 A * | 3/1999 | Lampotang et al. | 137/93 |
| 5,918,596 A * | 7/1999 | Heinonen | 128/204.21 |
| 5,924,418 A | 7/1999 | Lewis | |
| 5,934,274 A | 8/1999 | Merrick et al. | |
| 5,970,801 A | 10/1999 | Ciobanu et al. | |
| 6,001,332 A | 12/1999 | Garrett | |
| 6,085,743 A * | 7/2000 | Rosen et al. | 128/200.24 |
| 6,089,226 A | 7/2000 | Gier | |
| 6,089,229 A * | 7/2000 | Bathe et al. | 128/204.21 |
| 6,138,670 A | 10/2000 | Delauze et al. | |
| 6,142,147 A * | 11/2000 | Head et al. | 128/204.21 |
| 6,196,222 B1 | 3/2001 | Heinonen et al. | |
| 6,253,765 B1 | 7/2001 | Hognelid et al. | |
| 6,302,106 B1 | 10/2001 | Lewis | |
| 6,305,212 B1 * | 10/2001 | Drzewiecki | 73/23.2 |
| 6,363,772 B1 | 4/2002 | Berry | |
| 6,962,154 B2 * | 11/2005 | Krebs | 128/203.12 |
| 7,089,927 B2 * | 8/2006 | John et al. | 128/200.24 |
| 2002/0169385 A1 * | 11/2002 | Heinonen et al. | 600/531 |

* cited by examiner

| Humidity, Gas Composition, Temperature and Barometric Pressure Table |||||||||||
|---|---|---|---|---|---|---|---|---|---|---|
| Conditions at Calibration |||||  Actual Conditions |||||  Correction Factor |
| $O_2$ (%) | RH (%) | BP (psia) | T (°F) | He (%) | $O_2$ (%) | RH (%) | BP (psia) | T° (F) | He (%) | |
| 21 | 0 | 14.7 | 77 | 0 | 21 | 0 | 14.7 | 77 | 0 | 1 |
| 21 | 0 | 14.7 | 77 | 0 | 21 | 0 | 14.2 | 77 | 0 | 1.017453325 |
| 21 | 0 | 14.7 | 77 | 0 | 21 | 0 | 13.9 | 77 | 0 | 1.028374424 |
| 21 | 0 | 14.7 | 77 | 0 | 21 | 0 | 13.1 | 77 | 0 | 1.059309872 |
| 21 | 0 | 14.7 | 77 | 0 | 21 | 0 | 12.2 | 77 | 0 | 1.097687584 |
| 21 | 0 | 14.7 | 77 | 0 | 21 | 0 | 11.3 | 77 | 0 | 1.140563438 |
| 21 | 0 | 14.7 | 77 | 0 | 21 | 0 | 10.5 | 77 | 0 | 1.183215957 |
| 21 | 0 | 14.7 | 77 | 0 | 21 | 0 | 7.4 | 77 | 0 | 1.409427716 |
| 21 | 0 | 14.7 | 77 | 0 | 25 | 0 | 14.7 | 77 | 0 | 0.997359741 |
| 21 | 0 | 14.7 | 77 | 0 | 30 | 0 | 14.7 | 77 | 0 | 0.994088639 |
| 21 | 0 | 14.7 | 77 | 0 | 35 | 0 | 14.7 | 77 | 0 | 0.990849512 |
| 21 | 0 | 14.7 | 77 | 0 | 40 | 0 | 14.7 | 77 | 0 | 0.987641844 |
| 21 | 0 | 14.7 | 77 | 0 | 45 | 0 | 14.7 | 77 | 0 | 0.984465128 |
| 21 | 0 | 14.7 | 77 | 0 | 50 | 0 | 14.7 | 77 | 0 | 0.981318869 |
| 21 | 0 | 14.7 | 77 | 0 | 55 | 0 | 14.7 | 77 | 0 | 0.978202585 |
| 21 | 0 | 14.7 | 77 | 0 | 60 | 0 | 14.7 | 77 | 0 | 0.975115801 |
| 21 | 0 | 14.7 | 77 | 0 | 65 | 0 | 14.7 | 77 | 0 | 0.972058056 |
| 21 | 0 | 14.7 | 77 | 0 | 70 | 0 | 14.7 | 77 | 0 | 0.969028896 |
| 21 | 0 | 14.7 | 77 | 0 | 75 | 0 | 14.7 | 77 | 0 | 0.966027881 |
| 21 | 0 | 14.7 | 77 | 0 | 80 | 0 | 14.7 | 77 | 0 | 0.963054575 |
| 21 | 0 | 14.7 | 77 | 0 | 85 | 0 | 14.7 | 77 | 0 | 0.960108555 |
| 21 | 0 | 14.7 | 77 | 0 | 90 | 0 | 14.7 | 77 | 0 | 0.957189408 |
| 21 | 0 | 14.7 | 77 | 0 | 95 | 0 | 14.7 | 77 | 0 | 0.954296726 |
| 21 | 0 | 14.7 | 77 | 0 | 100 | 0 | 14.7 | 77 | 0 | 0.951430111 |
| 21 | 0 | 14.7 | 77 | 0 | 21 | 0 | 14.7 | 50 | 0 | 0.974520268 |
| 21 | 0 | 14.7 | 77 | 0 | 21 | 0 | 14.7 | 60 | 0 | 0.984034135 |
| 21 | 0 | 14.7 | 77 | 0 | 21 | 0 | 14.7 | 70 | 0 | 0.993456895 |
| 21 | 0 | 14.7 | 77 | 0 | 21 | 0 | 14.7 | 80 | 0 | 1.002791119 |
| 21 | 0 | 14.7 | 77 | 0 | 21 | 0 | 14.7 | 90 | 0 | 1.012039254 |
| 21 | 0 | 14.7 | 77 | 0 | 21 | 0 | 14.7 | 98 | 0 | 1.019377355 |
| 21 | 0 | 14.7 | 77 | 0 | 21 | 25 | 14.7 | 98 | 0 | 1.022321589 |
| 21 | 0 | 14.7 | 77 | 0 | 21 | 50 | 14.7 | 98 | 0 | 1.025291482 |
| 21 | 0 | 14.7 | 77 | 0 | 21 | 75 | 14.7 | 98 | 0 | 1.028287409 |
| 21 | 0 | 14.7 | 77 | 0 | 21 | 100 | 14.7 | 98 | 0 | 1.031309753 |

Fig. 5

GAS IDENTIFICATION SYSTEM AND VOLUMETRICALLY CORRECT GAS DELIVERY SYSTEM

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

The present invention relates generally to a patient ventilation system, and more particularly, to a gas identification (ID) and a volumetrically corrected gas delivery system applied to a ventilation system.

Ventilation treatments have been used as a therapeutic intervention to relieve dyspnea for a patient in acute respiratory distress directly related to severe increases in airway resistance. For moving gas into and out of the lungs, an open airway for the gas to flow from the higher pressure zone to the lower pressure zone is required. The greater the pressure between two points of the airway, the greater volume of gas is moved within the airway. The pressure in airway is directly related to the dynamic pressure gradient during the respiratory cycle, the flow rate of the gas, the density and viscosity of the gas, and the caliber and length of the airway.

Being an inert gas, helium does not participate or interfere with any biochemical process of the body. That is, helium itself has no curative value and cannot support life. However, as helium is the second lightest gas, it is often mixed with oxygen to decrease the gas density, so as to decrease the amount of pressure required for moving gas through the airway. For clinical application, helium typically is mixed with at least 21% oxygen due to its lack of pharmacological properties.

According to specific condition of each patient, the composition of the mixture of helium and oxygen (heliox) is altered. For example, when the patient is in need of a higher concentration of oxygen, a higher driving pressure is required for delivering the gas to the patient. On the contrary, when a lower concentration of oxygen is needed by the patient, the concentration of helium can be increased to dilute the oxygen, and to thereby reduce the required driving pressure of the gas. In order for the therapist/clinician to effectively provide adequate ventilation in obstructive disease patients such as chronic obstructive pulmonary disease or asthma, it is imperative that the clinician understands the relationship between airway resistance and gas characteristics.

Prior art ventilating systems that supply oxygen to a patient normally have two gas inlets, one of which is connected to an oxygen source, and the other is connected to a second gas source. Heliox with 80% of helium and 20% of oxygen, heliox with 70% of helium and 30% of oxygen, or air (with 21% of oxygen and 78% of nitrogen) are frequently applied as the second gas in such ventilating systems. After entering the ventilating system, oxygen and the second gas are mixed in a blender. According to the specific condition of the patient, the fractional inspiratory oxygen flow rate ($FIO_2$) of the gas mixture (oxygen and the second gas) is set by the clinician, and the volumes of oxygen and the second gas entering and exiting the blender are controlled to provide an adequate oxygen flow rate ($FIO_2$) to the patient. However, such adjustment may be inaccurate when the gas composition is altered. For example, when one applies heliox with 80% of helium and 20% of oxygen to a ventilating system of which the blender is driven according to the volumetric flow of heliox with 70% helium and 30% oxygen, the actual $FIO_2$ air or oxygen flow rate is very likely lower than the clinician set value. In addition to obtaining an ineffective ventilation, such inaccuracy may cause a life threatening event, especially when a patient is in critical condition.

Being controlled by the blender, the gas mixture is then delivered to the patient. Again, the exact gas flow rate delivered to the patient is critical. Therefore, a flow sensor is typically installed in the prior art on the inspiratory circuit of the ventilating system to ensure that an adequate rate of gas is flowing to the patient. Similarly, the expiratory flow is also typically monitored and controlled in the prior art via a flow sensor installed in the expiratory flow circuit. To obtain an accurate measurement of the oxygen flow rate, the blender and the flow meters are calibrated before being used. However, the blender and the flow meters incorporated in the conventional prior art ventilating system are calibrated for air instead of the exact gas composition supplied by the ventilating system. This again suppresses the desired oxygen delivery effectiveness of the ventilation system. When the patient is under a critical condition, such delivery ineffectiveness and/or inaccuracy may endanger the patient.

Therefore a substantial need exists in the art to provide a gas ID that can automatically and reliably detect the exact kind of gas supplied to a ventilating system, so as to provide an exact oxygen flow rate required by the patient. Further, correction for calibration of the blender and the flow sensors is also needed to appropriately assist the property prescribed respiration therapy of the patient.

BRIEF SUMMARY OF THE INVENTION

The present invention provides an automatic electronic gas identification ID, which preferably comprises a gas inlet and a voltage divider attached on the gas inlet of the ventilator. The gas inlet interlocks a gas source such as a conventional gas bottle or tank with the gas delivery system. When the gas is supplied to the gas delivery system, the voltage divider is inserted, i.e., plugged in to the ventilator. The voltage divider includes a resistor, across which a voltage drop is measured to identify the actual gas composition supplied to the gas delivery system. A lookup table in which a list of voltage drop values corresponding to the various gases used in ventilation therapy is stored is further included. Once the voltage drop is measured, the corresponding gas is determined from the lookup table to provide an automatic fail-safe identification of the actual gas composition supplied to the ventilator.

The present invention further provides a blender applied to a gas delivery system to blend a gas and oxygen supplied therein. The blender is driven by an actuator preferably implemented as a stepper motor for driving the blender to various blending positions according to a desired oxygen flow rate of a mixture of the gas and oxygen. The blender positions are calibrated based on characteristics of the gas, such as the specific heat ratio and the gas constant.

The present invention also provides one or more flow sensors installed in a gas delivery system to detect a flow rate of a mixture of a gas and an oxygen delivered and/or expelled by the gas delivery system. The flow sensor is calibrated according to temperature, humidity, barometer pressure and composition of the gas. When the flow rate of the gas drops under a certain value, the viscous force dominate the flow rate.

Therefore, the viscosity of the gas has to be considered as a factor in the calibration of the flow sensor.

The gas delivery system of the present invention includes a ventilating system, which comprises two gas inlets, with one connected to an oxygen source and the other one connected to a gas source, the gas ID, the blender and one flow sensor installed in an inspiratory circuit, a proximal circuit, and an expiratory circuit thereof. A flow control valve may also be installed on the inspiratory circuit to adjust the flow rate according to reading of the inspiratory flow sensor. The inspiratory flow sensor, the proximal flow sensor and the expiratory flow sensor are calibrated based on a reference volumetric flow calculated at a body temperature, a gas constant of air, and a barometric pressure. Such reference volumetric flow is pre-stored in a calibration table.

Accordingly, methods of correcting the calibration of the blender and the flow sensor for gas composition are also provided by the present invention. In the method of correcting calibration of the blender, the oxygen flow rate in air is calibrated as a multiplication factor of a blender position for air. A volumetric flow ratio of a gas supplied to the blender to the air is derived. The multiplication factor for air is substituted with a factor derived from the gas volumetric flow ratio of the gas, a volume fraction of oxygen in the gas, and an oxygen flow rate of the gas. The volumetric flow ratio is determined by gas constants and specific heat ratios for air and the gas.

In the method of correcting the calibration of a flow sensor, a standard volumetric flow for air with 21% of oxygen at an ambient pressure and temperature is derived. The standard volumetric flow for air is then converted into a reference volumetric flow for air under a body temperature and a standard pressure. The standard volumetric flow is then multiplied by a correction factor derived according to actual temperature, humidity, pressure and a gas constant of the gas applied to the flow sensor.

BRIEF DESCRIPTION OF THE DRAWINGS

These, as well as other features of the present invention, will become more apparent upon reference to the drawings wherein.

DETAILED DESCRIPTION OF THE INVENTION

Figure 1:
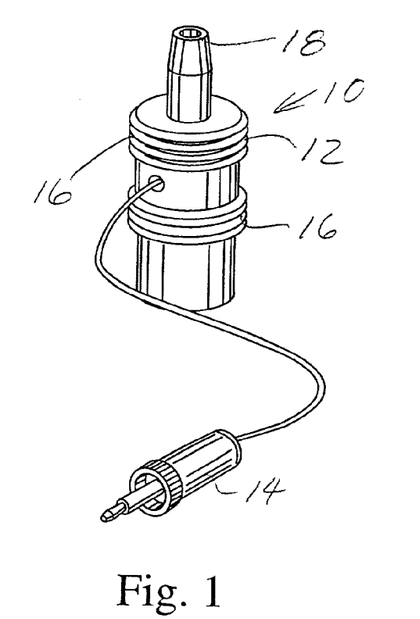
FIG. 1 shows the perspective view of a gas identifier used in a ventilating system according to the present invention.
Figure 2:
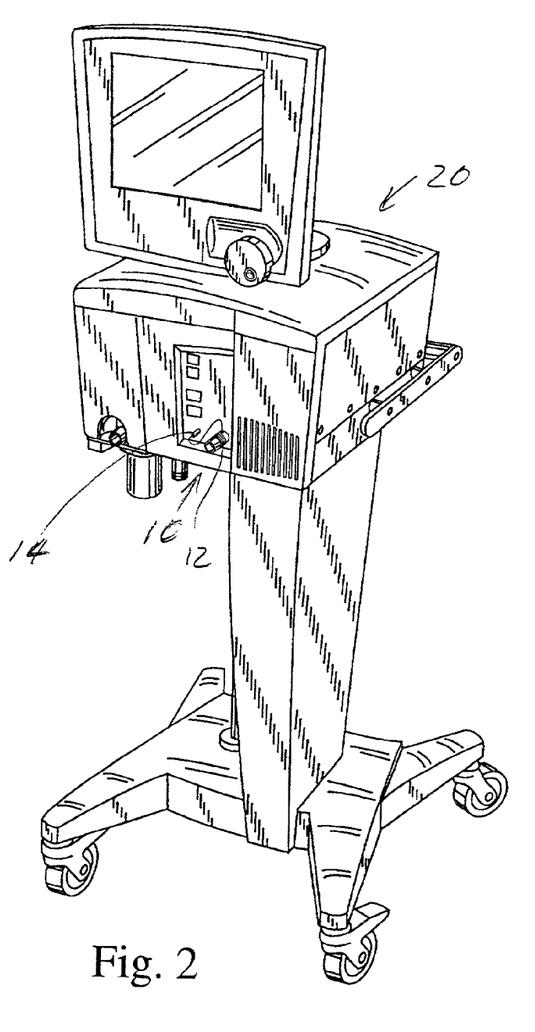
FIG. 2 shows the application of the gas identifier to a ventilator.

FIG. 1 shows a perspective view of a gas identifier 10 provided by the present invention. As shown in FIG. 1, the gas identifier 10 comprises a gas inlet 12 and a voltage divider 14 adapted to provide a pneumatic and electrical interface to the gas delivery system, i.e., ventilator 20 of the present invention. The gas inlet 12 interlocks to a conventional gas source such as a gas tank (not shown) and with the gas delivery system ventilator 20 as shown in FIG. 2. As is well known, conventional gas tanks providing different gas sources are supplied with standardized pneumatic connection terminals formed in conformity with either United States and/or European standards having differing thread and/or diameter sizes which uniquely identify the particular gas composition of the gas supply. The threads 16 or thread diameter on one end of the gas inlet 12 can be made in differing sizes to match the standardized size and configuration for the standardized pneumatic connection terminal. The other end 18 of the gas inlet 10 is formed to be inserted into the gas delivery system 20. The voltage divider 14 is tethered to the gas identifier 10 and is also selectively electrically connectable to the gas delivery system 20. The voltage divider 14 preferably includes a resistor having a resistance value unique for each gas supply composition and a lookup table. When the voltage divider 14 is inserted, i.e., plugged into the delivery system 20, the voltage drop there across is measured. For a particular gas, a corresponding voltage drop will result as measured across the resistor. For example, when heliox with 80% of oxygen and 20% of helium (referred as 80/20 heliox hereinafter) is connected to the gas delivery system, a voltage drop of 2.048V±5% across the resistor is expected. Alternatively, when heliox with 70% of oxygen and 30% of helium (referred as 70/30 heliox hereinafter) or an air is supplied to the gas delivered system 20, the voltage drop across the resistor is expected as 1.024V±5% or 4.096V±5%, respectively. The lookup table is then called up by the onboard processor used to control ventilator operation (not shown) of the gas delivery system 20 when a voltage drop is measured across the resistor. The lookup table comprises a list of the corresponding voltage drops across the voltage divider for various gases. By measuring the voltage drop across the resistor, the type of gas mapping with the voltage drop is obtained from the lookup table. When a new type of gas is provided, the lookup table can be reprogrammed to include the corresponding voltage drop of the new type of gas, so that the exact type of gas supplied to the gas delivery system can always be monitored and identified by the gas ID. An indicator or a display may be incorporated to display or show the type of gas identified by the gas ID. Thereby, one can monitor the exact type gas supplied to the gas delivery system 20 and the patient, so that the accuracy of oxygen flow rate ($FIO_2$) measured subsequently can be confirmed.

An automatic alarm system may also be utilized in the present invention. As will be recognized, the onboard processor may be configured to allow the clinician inputting the type of gas required by the ventilating system. Once the gas source is connected, the gas ID automatically identifies the gas supply. When the identified result is different from the input gas, an alarm signal or warning indication may be initiated. Alternatively, operation of the system may be halted when a differing gas is connected. Further, an adaptor or a connector may be used to allow the gas ID connecting different gas sources to the system.

Figure 3:
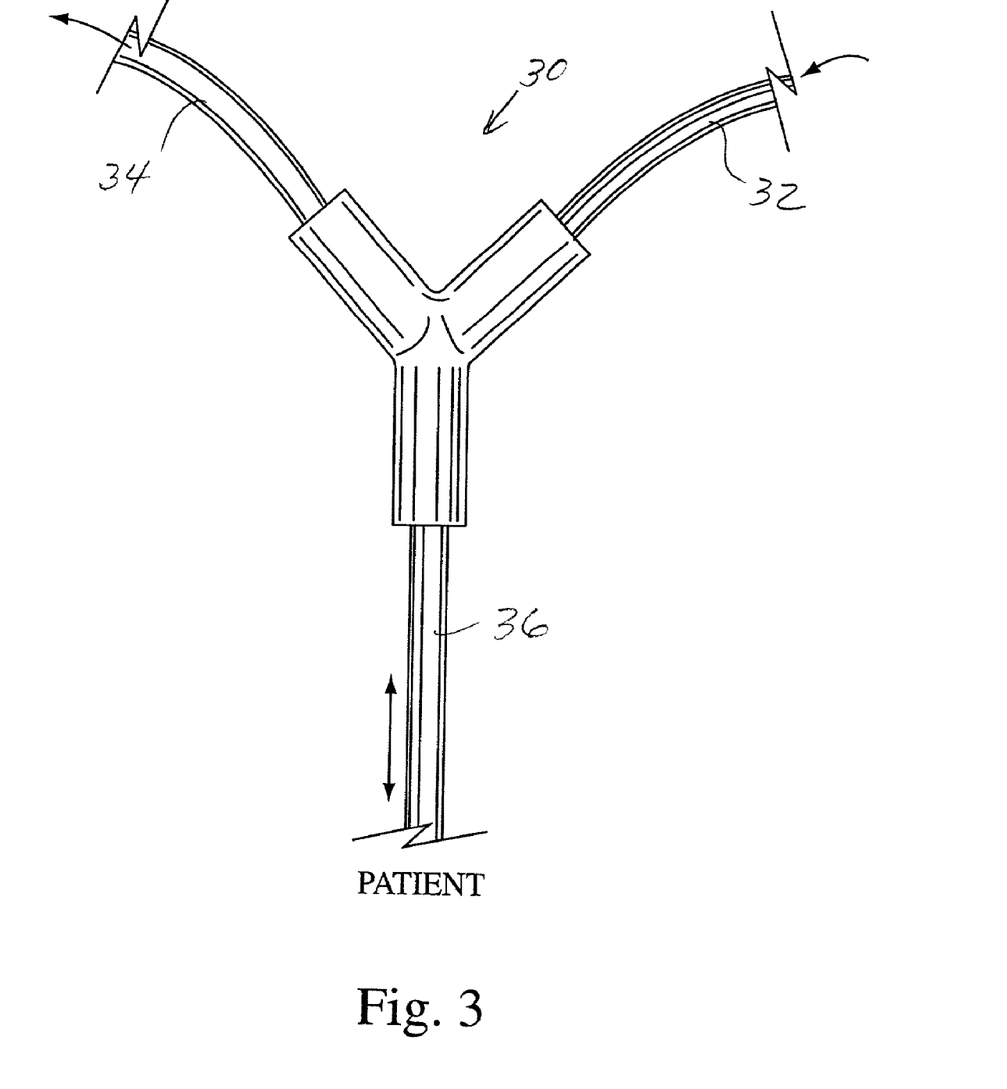
FIG. 3 shows a Y-shape heliox administration.

FIG. 3 depicts a schematic drawing of the inspiratory, expiratory and proximal circuit portions of a gas delivery system 30 which supplies ventilation gas to the patient and allows exhalation of gas from the patient through monitored time periods; volumes; pressures and flow rates. The gas delivery system 30 includes the inspiratory circuit 32, an expiratory circuit 34, and a proximal circuit 36 directly applied to the patient. Along each of these three portions, a conventional flow sensor is preferably installed to monitor the oxygen flow rate $FIO_2$ and exhalation flow rate. Although not by way of limitation, in the preferred embodiment, such flow sensors comprise a variable orifice flow sensor similar to that defined in U.S. Pat. No. 4,993,269 issued to Guillaume, et al., entitled Variable Orifice Flow Sensing Apparatus, the disclosure of which is expressly integrated herein by reference. The proximal circuit 36 can be administered with a mask, a mouth piece, a nasal cannula, a hood, or other conventional equipment, according to the specific condition of the patient.

Figure 4:
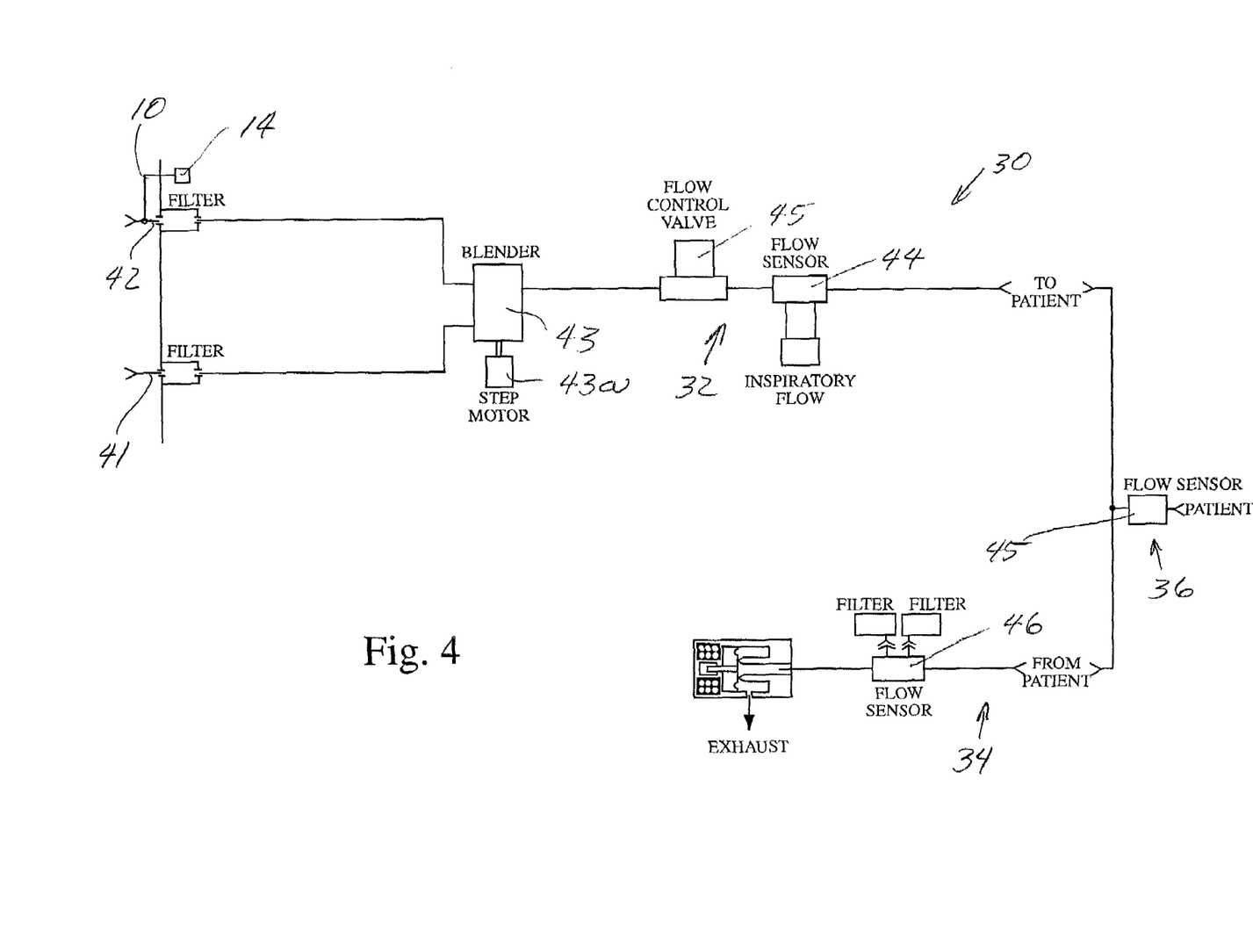
FIG. 4 shows the respiratory circuit of the patient.

FIG. 4 depicts the pneumatic circuit diagram of the gas delivery system 30 of the present invention. As shown in FIG.

4, an oxygen gas inlet 41 is connected to an oxygen source, while a gas inlet 42 is connected to a second gas such as 80/20 heliox, 70/30 heliox, 65/35 heliox, air, nitrox (a mixture of nitrogen and oxygen) or trimox (a mixture of helium, nitrogen and oxygen), or other gas that assists the patient to breathe. Again, a gas ID 10 is also plugged in via voltage divider 14 to the gas delivery system 30 to identify the second gas. The oxygen and gas are then delivered to a blender 43 which is driven by an actuator, preferably a stepper motor 43a. The stepper motor 43a drives the blender position step by step according to the oxygen flow rate (FIO$_2$) set up, i.e., manually selected by the clinician and the specific type of gas supplied to the blender 43 in addition to oxygen. More specifically, the blender position driven by an actuator such as the stepper motor 43a is different when the oxygen flow rate changes and/or the supplied gas is different, therefore, the blender 43 has to be calibrated for the particular delivered gas mixture before operation. However, since the blender 43 incorporated in the gas delivery system is typically only calibrated based on air, a further correction for various types of gases supplied to the gas delivery system is therefore required. A further description of the calibration algorithm utilized in the present invention will be provided infra.

Being blended by the blender 43, the gas mixture is the delivered along the inspiratory circuit 32 to the patient. As mentioned above, under different condition or for different patients, the required gas flow rate is different. Therefore, it is crucial to monitor whether the actual delivered gas flow rate is maintained as predetermined. A flow sensor 44 is thus installed along the inspiratory circuit 32. A flow control valve 45 can also be installed to adjust the gas flow when the reading of the flow sensor 44 is different from the desired pre-set value. In the preferred embodiment of the present invention, the flow sensor 44 measures the pressure drop that is directly related to the gas flow rate across an orifice thereof. The pressure drop is transferred into an electronic signal, and the voltage of the electronic signal directly reflects the gas flow rate of the gas mixture. Again, the voltage that reflects the gas flow rate is different depending on the gas type. Thus, the flow sensor 44 must be calibrated according to the exact gas mixture before being used to provide a correct reading. As previously stated, typically, the flow sensor is initially calibrated for air only. Therefore, when a gas mixture other than air flows through the flow sensor, the calibration of the flow sensor 44 has to be corrected based on the characteristics of the particular gas mixture and the actual delivery conditions. Similarly, flow sensors 45 and 46 are also installed at the port of the proximal circuit 36 directly applied to the patient and the expiratory circuit 34 through which the patient exhales to properly monitor the respiration. As with the inspiratory circuit flow sensor 44, the proximal and expiratory flow sensors 45 and 46 typically initially calibrated for air must be recalibrated/corrected based upon the particular gas mixture and respiratory conditions. The preferred correction of calibration of the blender 43 and each of the flow sensors 42, 44 and 46 will be introduced as follows:

In the following paragraphs, correction of calibration for the blender 43 position and the flow sensors 44, 45 and 46 are introduced using heliox mixture as an example. The correction for gas mixture other than heliox such as for nitrogen and/or carbon dioxide can be derived by the same algorithm. For the air containing about 21% of oxygen, the oxygen flow rate of the air mixture (of oxygen and air) can be represented as:

$$FIO_2|_{Air} = \frac{Q_{O_2} + 0.21 Q_{Air}}{Q_{O_2} + Q_{Air}} \quad (1)$$

where Q stands for volumetric flow of the gas subscript thereunder. Assuming that the oxygen percentage of heliox is $vf_{He}$, the oxygen flow rate in heliox mixture can be represented as:

$$FIO_2|_{Heliox} = \frac{Q_{O_2} + vf_{He} \cdot Q_{Heliox}}{Q_{O_2} + Q_{Heliox}} \quad (2)$$

When the orifice and pressure drop across the blender 43 are the same, the volume metric flow ratio, that is, the flow correction factor $F_r$, of the heliox mixture (heliox and oxygen) in the blender can be represented as:

$$\frac{Q_{Heliox}}{Q_{Air}} = F_r = \sqrt{\frac{R_{Heliox} \cdot \gamma_{Heliox} \cdot (\gamma_{Air} - 1)}{R_{Air} \cdot \gamma_{Air} \cdot (\gamma_{Heliox} - 1)} \cdot \frac{\left[\left(\frac{P_2}{P_1}\right)^{2/\gamma_{Heliox}} - \left(\frac{P}{P_1}\right)^{(\gamma_{Heliox}+1)/\gamma_{Heliox}}\right]}{\left[\left(\frac{P_2}{P_1}\right)^{2/\gamma_{Air}} - \left(\frac{P}{P_1}\right)^{(\gamma_{Air}+1)/\gamma_{Air}}\right]}} \quad (3)$$

Where R and γ are the gas constant and the specific heat ratio of the gases subscript thereunder, respectively, and $P_1$ and $P_2$ are the upstream and downstream pressures, respectively. While blending air with oxygen, the oxygen flow rate of air and the blender position are in a linear correlation as:

$$FIO_2|_{Air} = 0.21 + \frac{Sp}{S_{max}} \cdot 0.79 \quad (4)$$

Where Sp is the blender position in steps of the actuator stepper motor 43a, and $S_{max}$ is the maximum steps or total steps of the stepper motor 43a stored in an electrical erasable and programmable read only memory (EEPROM) incorporated into the blender. The above equation (4) can be transformed into:

$$Sp = (FIO_2|_{Air} - 0.21) \cdot S_{max} \cdot 1.266 \quad (5)$$

Table 1 shows the corresponding gas constants, specific heat ratios, and volume fractions of the gas, and Table 2 shows the corresponding flow correction factors for various upstream pressures and downstream pressures of heliox with different volume ratios.

TABLE 1

| Gas Composition | Air | 80/20 Heliox | 70/30 Heliox | 65/35 Heliox |
|---|---|---|---|---|
| Gas Constant R | 53.3522 | 160.92 | 124.597 | 111.961 |
| Specific Heat Ratio γ | 1.40 | 1.58 | 1.55 | 1.535 |
| $vf_{He}$ | — | 0.20 | 0.30 | 0.35 |

TABLE 2

| $P_1$ (psig) | $P_2$ (psig) | Fr (80/20 Heliox) | Fr (70/30 Heliox) | Fr (65/35 Heliox) |
|---|---|---|---|---|
| 11.5 | 6.7 | 1.758 | 1.544 | 1.463 |
| 11.5 | 9.3 | 1.746 | 1.535 | 1.455 |
| 11.5 | 11.4 | 1.737 | 1.528 | 1.449 |
| 10.8 | 6.1 | 1.759 | 1.545 | 1.463 |
| 10.8 | 8.6 | 1.746 | 1.535 | 1.455 |
| 10.8 | 10.7 | 1.737 | 1.528 | 1.449 |
| Fr | Fr | 1.746 | 1.535 | 1.455 |

Therefore, when the gases supplied to the blender 43 includes a mixture of oxygen and heliox instead of a mixture of oxygen and air, the blender position should be controlled in relation to $(FIO_2|_{Heliox})$ instead of $(FIO_2|_{Air})$, and the blender position as shown in Equation (4) can be modified as:

$$Sp = \left[ \frac{((FIO_2|)_{Heliox} - vf_{He}) \cdot Fr + 0.21 \cdot ((1 - FIO_2|)_{Heliox})}{((FIO_2|)_{Heliox} - vf_{He}) \cdot Fr + ((1 - FIO_2|)_{Heliox})} - 0.21 \right] \cdot S_{max} \cdot 1.266 \quad (5)$$

From Tables 1 and 2, $vf_{He}$ standing for volume fraction of oxygen is 0.2 for 80/20 heliox mixture, 0.3 for 70/30 heliox mixture and 0.35 for 65/35 heliox mixture. The Fr standing for the flow correction factor is 1.746, 1.535 and 1.455 for 80/20, 70/30, 65/35 heliox mixture, respectively. Therefore, by controlling the blender position which has been corrected for the particular gas mixture, the exact amount of oxygen flow rate in the gas mixture can be controlled. Again, the flow correction $F_r$ and volume fraction of oxygen for the corresponding gas can be pre-stored in a lookup table. When the oxygen flow rate for a particular gas mixture is selected, the lookup table is called up, the blender position automatically corrected, and the exact oxygen flow rate is provided.

Based on gas dynamics theory, a general correction factor for the variable orifice flow sensors 32, 34 and 36 is related to gas temperature, relative humidity, barometer pressure (including back pressure) and gas composition. In addition, such variable orifice flow sensor measure the pressure drop across the orifice ($\Delta P$) as a function of volumetric flow. However, under different conditions (that is, when any of the above correction factors is altered), same orifice geometry and $\Delta P$ may represent different flow. Therefore, the flow sensors have to be corrected under different conditions before being used for specific respiratory measurements.

For a perfect gas and isentropic gas flow, the mass flow can be expressed as:

$$W = \frac{c \cdot A \cdot P}{\sqrt{T_1}} \cdot \sqrt{\frac{2 \cdot \gamma \cdot g}{(\gamma-1) \cdot R} \cdot \left[ \left(\frac{P_2}{P_1}\right)^{2/\gamma} - \left(\frac{P_2}{P_1}\right)^{(\gamma+1)/\gamma} \right]} \quad (6)$$

Where A is the effective area of the orifice of the flow sensor, P is the absolute pressure (the subscript "1" indicates for upstream and "2" indicates for downstream), $T_1$ is the upstream temperature in °K or °R, R is gas constant, $\gamma$ is the specific heat ratio, and g is the gravitation acceleration. The typical flow sensor produces a pressure drop $\Delta P$ no more than 10 cmH$_2$O, and the upstream and downstream pressures have the following relationship.

$$\frac{P_2}{P_1} = \frac{P_2}{P_2 + \Delta P} = 1 - \frac{\Delta P}{P_2} + O\left(\frac{\Delta P^2}{P_2^2}\right) \quad (7)$$

The pressure drop across the flow sensor $\Delta P$ is equal to difference between the upstream and the downstream pressures, that is, $P_1 = P_2 + \Delta P$. The second and higher orders incurring an error of only 0.01%, that is, [0.147 psi/{0.147 psi)2], are neglected, so that the Equation (6) can be expressed as:

$$W \cong \frac{c \cdot A \cdot P_1}{\sqrt{T}} \cdot \sqrt{\frac{2 \cdot \gamma \cdots g}{(\gamma-1) \cdot R} \cdot \left[ \left(1 - \frac{\Delta P}{P_2}\right)^{2/\gamma} - \left(1 - \frac{\Delta P}{P_2}\right)^{(\gamma+1)/\gamma} \right]} \quad (8)$$

$$\cong \frac{c \cdot A \cdot P_1}{\sqrt{T}} \cdot \sqrt{\frac{2 \cdot \gamma \cdots g}{(\gamma-1) \cdot R} \cdot \left[1 - \frac{2}{\gamma} \cdot \frac{\Delta P}{P_2} - 1 + \frac{\gamma+1}{\gamma} \cdot \frac{\Delta P}{P_2}\right]}$$

Since $W = \rho_1 Q$ and $P_1 = \rho_1 RT_1$, so that $$Q = c \cdot A \cdot \sqrt{\frac{2 \cdot g \cdot R \cdot T_1 \cdot \Delta P}{P_2}} \quad (9)$$

When the condition A ($T_A$ in °K or °R, $R_A$, $P_{2A}$) results in the same pressure drop across the same flow sensor as the condition B ($T_B$ in °K or °R, $R_B$, $P_{2B}$) does, the volumetric flow under conditions A and B have the relationship as:

$$\frac{Q_A}{Q_B} = \sqrt{\frac{R_A \cdot T_A \cdot P_{2B}}{R_B \cdot T_B \cdot P_{2A}}} \quad (10)$$

The gas constant can be calculated by:

$$R = \frac{R_u}{\sum_{i=1}^{n} vf_i \cdot M_i} \quad (11)$$

Where $R_u$ is the universal gas constant equal to 1545.32 ft-Lb/Lbm-mol° R, $M_i$ is the molecular weight of each component of the gas, and $vf_i$ is the volume fraction of each component. Table 3 lists the molecular weight of gases common applied to the ventilating system.

TABLE 3

| | Component | | | |
|---|---|---|---|---|
| | O2 | N2 | H2O | He |
| Molecular Weight | 31.999 | 28.1599 | 18.0153 | 4.004 |

As mentioned above, the pressure drop across the flow sensor is directly related to the humidity, therefore, the vapor pressure of the gas needs to be calculated for calibration of the flow sensor. A humidifier is typically installed into gas delivery system to provide a certain percentage, preferably 100%, of humidity to the patient. The volume fraction of H$_2$O vapor can be obtained from:

$$vf_{vap} = P_{vap}/P$$

$$P_{vap} = P_{vapsat} \cdot RH \quad (12)$$

Where $P_{vap}$ is the vapor pressure, RH is the relative humidity, $P_{vapsat}$ is the saturation vapor pressure (with 100% of RH), and P is the current barometric pressure. Within the temperature range of 32 to 392° F., the saturation vapor pressure $P_{vapsat}$ can be obtained empirically by:

$$P_{vapsat} = \exp\left[C_6 \cdot \ln(T) + \sum_{i=1}^{5} C_i \cdot T^{i-2}\right] \quad (13)$$

Where
$C_1 = -1.0440397 \times 10^4$
$C_2 = -1.1294650 \times 10^1$
$C_3 = -2.7022355 \times 10^{-2}$
$C_4 = 1.2890360 \times 10^{-5}$
$C_5 = -2.4780681 \times 10^{-9}$
$C_6 = 6.5459673$, and T is in ° R. Consequently, the volume fraction $vf_{iDry}$ for other components in the gas mixture can be obtained from:

$$vf_i = vf_{iDry}(1 - vf_{vap}) \quad (13)$$

Figure 5:
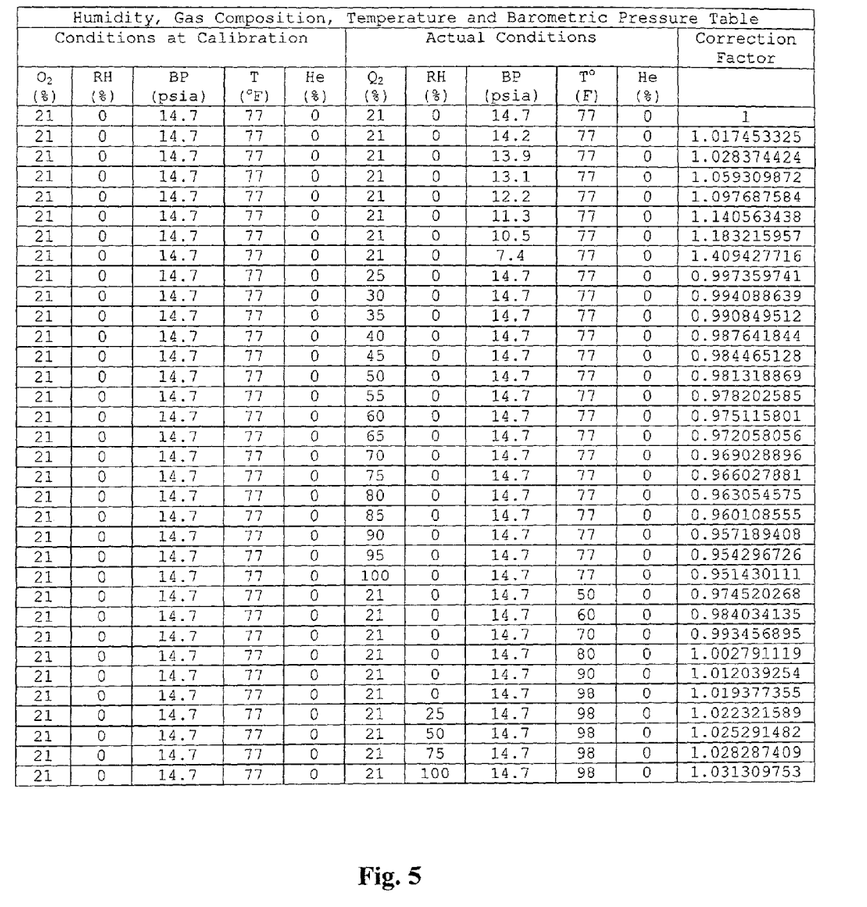
FIG. 5 shows a table of correction factors under various conditions.

FIG. 5 shows a table listing the sample calculation of correction factors by assuming that a perfect, isentropic flow gas is delivered and a small pressure drop is produced by the orifice. Under normal environmental and physiological conditions, a perfect gas assumption is valid, and the same is also true for most environmental conditions. For example, referring to the second row of the table, when the barometer pressure is 14.2 psia instead of 14.7 psia at the sea level, the correction factor is 1.7% higher than 1. Therefore, whenever any of the above parameters changes, the correction has to be made to ensure the accuracy of the rate of the gas flowing to the patient.

However, the isentropic flow assumption is only valid when viscosity of the gas flow is negligible, which requires a high Reynolds number. For a 0.4 LPM (liter per minute) gas flowing in a one-inch pipe, the high Reynolds number requirement (Re=22) may not be valid. Therefore, Equations (9) and (10) must be validated with experimental results for low gas flow rates.

The volumetric flow ratio of conditions A to B in Equation (10) is equal to $(\rho_B/\rho_A)^{1/2}$ for a perfect gas. That is, the volumetric flow ratio is related to the density of the gas. This is consistent with the isentropic flow assumption in which inertia force dominates. On the other hand, if Reynolds number is low for a very low flow rate in the viscous force dominant condition, the volumetric flow ratio is viscosity µ related and can be expressed as $Q_A/Q_B = \mu_A/\mu_B$ according to Poiseulle law. For intermediate flow rates, both inertia and viscous force are present, an empirical equation for flow correction is in a form of:

$$\frac{Q_A}{Q_B} = Ca(Re) \cdot \sqrt{\frac{\rho_B}{\rho_A}} + Cb(Re) \cdot \frac{\mu_B}{\mu_A} \quad (14)$$

Where the flow rates for the same geometry Ca and Cb are functions of Re (the Reynolds number, that is, the flow rates for the same geometry). The viscous force dominant volumetric flow ratio and the correction of calibration for the flow sensors under the same condition will be discussed further after the introducing the correction of calibration for flow sensor installed along each of the inspiratory circuit, the expiratory circuit and the proximal circuit.

For variable orifice flow sensor installed along the inspiratory circuit, $$\frac{V_s}{V_c} = \sqrt{\frac{R_s \cdot T_s \cdot P_c}{R_c \cdot T_c \cdot P_s}} \quad (15)$$

Where V is the volumetric flow (which is the same as Q introduced previously), the subscript s stands for the actual conditions at the flow sensor, and the substrate c stands for the reference calibration conditions. After the flow sensor, the flow relation is governed by conservation of mass:

$$\frac{V_s}{V_f} = \frac{\rho_f}{\rho_s} = \frac{P_f \cdot R_s \cdot T_s}{P_s \cdot R_f \cdot T_f} \quad (16)$$

Where the substrate f refers the final properties, that is, the conditions at the patient's end. The flow sensor is calibrated at ATP (21% of $O_2$, ambient pressure and temperature) and corrected to CAL_STD_1 (which includes body temperature of 37° C., standard pressure 14.7 psia, and saturated vapor pressure). By substituting the molecular weight and the volume fraction for each component in the gas flowing through the flow meter (including oxygen, air and water) into Equation (11), the actual gas constant can be calculated as:

$$R_c = \frac{1545.32}{0.79 \cdot (1 - vf_{vap}) \cdot 28.1599 + 0.21 \cdot (1 - vf_{vap}) \cdot 31.999 + vf_{vap} \cdot 18.0153} \quad (17)$$

Where $vf_{vap} = P_{vap}/P_c$, and $P_{vap} = P_{vapsat}RH$ (Equation (12), where $P_c$ is the barometer pressure in psia, $P_{vap}$ is the vapor pressure and RH is the relative humidity and is assumed 0.15). The saturation vapor pressure can be calculated according to Equation (13) as:

$$P_{vapsat} = \exp\left[C_6 \cdot \ln(T_C) + \sum_{i=1}^{5} C_i T_C^{i-2}\right]$$

Where
$C_1 = -1.0440397 \times 10^4$
$C_2 = -1.1294650 \times 10^1$
$C_3 = -2.7022355 \times 10^{-2}$
$C_4 = 1.2890360 \times 10^{-5}$
$C_5 = -2.4780681 \times 10^{-9}$
$C_6 = 6.5459673$, $T_C$ is the ambient temperature in ° R and $P_C$ is the barometric pressure in psia.

In the practical application, the calibration conditions temperature ($T_C$), the gas constant ($R_C$) and the barometer pressure ($P_C$) may be different from the standard calibration condition (ATP). For example, for air mixture flowing through the flow sensor 44 installed along the inspiratory circuit 32, the calibration conditions $R_C$ is replaced by $T_B$ (which is 54.6078 for air), $T_C$ is replaced by $T_B$, which is the body temperature 557.67° R, and $P_C$ is replaced by $P_B$, which is 14.696 psia. The volumetric flow $V_C$ is thus converted into $V_B$, which is expressed as $$V_B = V_C \sqrt{\frac{R_B \cdot T_B \cdot P_C}{R_C \cdot T_C \cdot P_B}} \quad (18)$$

The value of $V_B$ can be stored in a calibration table of the EEPROM and called up as a reference to substitute $V_C$ in Equation (15).

By combining Equations (15) and (16), and substituting $P_f = P_{BAR}$, $P_s = P_{BAR} + P_{INSP}$ and $T_f = T_C = T_B = 37°$ C., $$F_{BTPS} = F_1 \cdot C1 \cdot C2 \cdot \sqrt{\frac{1}{T_{INSP}}} \cdot \sqrt{P_{BAR} + P_{INSP}} \quad (19)$$

Where
the subscript BTPS stands for body temperature, standard pressure and saturation vapor (100%);
$F_1$ is the volumetric flow $V_B$, which can be derived from the calibration table;
C1 has to be re-calculated by the following equation when the oxygen flow rate $FIO_2$ set up by the operator is changed, and/or the gas composition is changed (which is detected by the gas ID):

$$C1 = \frac{R_f}{P_{BAR} \cdot \sqrt{R_s}};$$

$$R_S = \frac{1545.32}{FIO_2 \cdot 31.9999 + (1 - FIO_2) \cdot M_g},$$

$M_g$ is the molecular weight for the gas, which is 4.003 for helium and 28.1599 for air;

$$R_f = \frac{1545.32}{(1 - vf_{vap}) \cdot FIO_2 \cdot 31.999 + (1 - vf_{vap}) \cdot (1 - FIO_2) \cdot M_g + 18.0153 \cdot vf_{vap}}$$

$$vf_{vap} = \frac{62.94}{P_{BAR}} \cdot RH_d$$

$P_{BAR}$ is the barometric pressure in ranging from 732-1076 cmH$_2$O input by the operator;
$RH_d$ is the device humidity (is 1.0 for active or 0.4 for HME);
C2 is a constant which can be derived from $$C2 = \sqrt{\frac{T_B \cdot P_B}{R_B}},$$

and
$T_B = 310.15°$ K,
$R_B = 54.6078$, and
$P_B = 1034$ cmH$_2$O;

$T_{INSP}$ (the same as $T_s$) is the temperature at FCV (flow control valve) in ° K which that can be read from an A/D converter and measured by a thermistor; and $P_{INSP}$ is the gauge pressure in the inspiratory circuit (in cmH$_2$O), ranging from 0-100 cmH$_2$O.

Therefore, when heliox gas mixture is supplied to the system, the flow sensor is corrected based on the characteristics of the heliox gas mixture. The reading of the flow sensor is $F_{BTPS}$ for heliox mixture instead of Fi for air. That is, the flow rate for air (Fi) should be multiplied by the correction factor in Equation (19) to provide the actual gas flow rate.

Helium is a gas that has a higher viscosity compared to air. Therefore, once the flow rate drops to a certain magnitude, the viscous force dominates. The correction for the flow sensor thus has to be converted from the density dominant format into the viscosity dominant. Such situation is also considered when other gas is applied to the system, however, the critical point for the conversion may be altered for different gas. In this embodiment, heliox mixture is used as an example to introduce the correction of the flow sensor when the viscous force dominates.

When a heliox mixture is applied to the system, the volumetric flow becomes viscosity dominant when the flow rate is lower than 4.06 LPM. Under such circumstance, an empirical relation is obtained as:

$$F_{BTPS} = F_r \cdot [A_1 \cdot f(F_1) + A_2 \cdot (1 - f(f_1))] \quad (20)$$

Where $$A_1 = C1 \cdot C2 \cdot \sqrt{\frac{1}{T_{INSP}}} \cdot \sqrt{P_{BAR} + P_{INSP}};$$

$$A_2 = \frac{(P_{INSP} + P_{BAR}) \cdot R_f \cdot T_B}{P_{BAR} \cdot R_S \cdot T_{INSP}} \cdot \frac{\mu_C}{\mu_S};$$

$\mu = 179.45$ (micro poise);

$$\mu_S = \frac{(1 - vf_{vap}) \cdot FIO_2 \cdot 31.999 \cdot \mu_{O_2} + (1 - vf_{vap}) \cdot (1 - FIO_2) \cdot M_g \cdot \mu_g + 18.0153 \cdot vf_{vap} \mu_{H_2O}}{(1 - vf_{vap}) \cdot FIO_2 \cdot 31.999 + (1 - vf_{vap}) \cdot (1 - FIO_2) \cdot M_g + 18.0153 \cdot v_{vap}};$$

$\mu_{O_2} = 44.2235 + 0.56243 \cdot T_{INSP} - 0.00011324 \cdot T_{INSP}^2$;
$\mu_g = 71.094 + 0.44318 \cdot T_{INSP} - 0.00005176 \cdot T_{INSP}^2$ for heliox;
$\mu_g = 42.6064 + 0.47525 \cdot T_{INSP} - 0.000098826 \cdot T_{INSP}^2$ for air;
$\mu_{H_2O} = -36.8255 + 0.42916 \cdot T_{INSP} - 0.00001624 \cdot T_{INSP}^2$; and
$f(F_1) = 0.2677 \cdot \ln(F_1) + 0.6724$.

Therefore, when the flow rate of heliox mixture is higher than 4.06 LPM, the flow rate is derived by Equation (19). However, when the flow rate drops to lower than 4.06 LPM, Equation (20) is used to calculate the flow rate.

The flow sensors located at the proximal circuit and the expiratory circuit can be calibrated and corrected by the same methods. However, as the calibration conditions of the flow sensors 45 and 46 located at the proximal 36 and the expiratory circuit 34 are normally different from those at the inspiratory circuit, the above parameters have to be adjusted. For the proximal-circuit, Equation (19) is modified as:

$$F_{BTPS} = F_Y \cdot C1 C2 \cdot \sqrt{P_{BAR} + P_Y} \quad (21)$$

Where $F_Y$ is the reference volumetric flow $V_B$, which can be obtained from the calibration table;

C1 and C2 are similar as Equation (19), however, the gas constant should be denoted as $R_Y$ instead of $R_s$, which is the gas constant of the gas mixture at the proximal circuit;

$$C1 = \frac{R_f}{P_{BAR} \cdot \sqrt{R_Y}}, \text{ and } C2 = \sqrt{\frac{P_B}{R_B}};$$

$$R_Y = \frac{1545.32}{(1-vf_{vapY}) \cdot FIO_2 \cdot 31.999 + (1-vf_{vapY}) \cdot (1-FIO_2) \cdot M_g + 18.0153 \cdot vf_{vapY}};$$

$$vf_{vapY} = \frac{62.94}{P_{BAR}}$$

during exhalation and $$vf_{vapY} = \frac{62.94}{P_{BAR}} \cdot RH_d$$

during inhalation;

$RH_d$ is 1.0 for active or 0.4 for HME;

$P_Y$ is the proximal pressure; and $P_S = P_{BAR} + P_{EXP}$, where $P_{EXP}$ is the gauge pressure of the expiratory circuit.

As shown from the above equation, the humidity of the proximal circuit 36 is different for inhalation and exhalation processes, therefore, the gas constant is varied. Further, as the proximal temperature is close to the body temperature, such that the factor of square root of $T_{INSP}$ is eliminated by the factor of square root of $T_B$ in C2.

For the expiratory circuit 34, the expiratory temperature normally drops from the body temperature to about 5.5° C. lower. This results in a drop of vapor volume fraction in the expiratory circuit. Therefore, with Ps=PBAR+PEXP and the other same conditions, $$F_{BTPS} = F_{EXP} \cdot C1 \cdot C2 \sqrt{P_{BAR} + P_{EXP}} \quad (22)$$

Where $F_{EXP}$ is $V_B$ which can be obtained from the lookup table;

$$C1 = \frac{R_f}{P_{BAR} \cdot \sqrt{R_E}};$$

$$R_E = \frac{1545.32}{(1-vf_{vape}) \cdot FIO_2 \cdot 31.999 + (1-vf_{vape}) \cdot (1-FIO_2) \cdot M_g + 18.0153 \cdot vf_{vape}};$$

$$vf_{vapf} = \frac{62.94}{P_{BAR}} \cdot RH_d;$$

$$vf_{vape} = \frac{45.95}{P_{BAR}}$$

for active (assuming a 5.5° C. drop in gas temperature from the proximal circuit); and $$vf_{vape} = \frac{25.18}{P_{BAR}}$$

for HME;

$RH_d$ is 1.0 for active or 0.4 for HME;

$P_{BAR}$, $RH_d$ are the same as above;

$$C2 = \sqrt{\frac{T_B \cdot P_B}{R_B \cdot T_{EXP}}},$$

where $T_{EXP}$ is 313.15° K; and $P_{EXP}$ is the pressure of the expiratory circuit (ranging from 0-100 cmH$_2$O)

Again, when the flow rate is lower than a certain magnitude, the viscosity dominates. The flow rate is then related to both the density and the viscosity of the gas. Equation (20) can also be applied to the calibration correction for the proximal circuit 36 and the expiratory circuit 34 flow sensors.

Indeed, each of the features and embodiments described herein can be used by itself, or in combination with one or more of other features and embodiment. Thus, the invention is not limited by the illustrated embodiment but is to be defined by the following claims when read in the broadest reasonable manner to preserve the validity of the claims.

What is claimed is:

1. A gas delivery system, comprising:
   a gas identifier, by which a gas supplied to the gas delivery system is automatically identified;
   a blender, blending oxygen and the gas to provide a gas mixture with a preselected oxygen flow rate;
   an actuator, driving the blender into various blending positions according to the oxygen flow rate of the gas mixture, wherein the blending positions of the blender are corrected based on characteristics of the gas mixture; and
   at least one flow sensor, to measure a flow rate of the gas mixture, wherein the flow sensor is corrected based on the characteristics of the gas mixture.

2. A ventilating system, comprising:
   at least two gas inlets, with one inlet connected to an oxygen source and the other one connected to a gas source;
   a gas identifier, attached to the gas inlet connected to the gas source to identify a gas supplied therefrom;
   a blender, blending the oxygen and the gas into a mixture, wherein the blender is driven by an actuator into various positions according to a selected oxygen flow rate of the mixture, and the blender positions are calibrated based on the specific heat ratio and gas constant of the gas;
   an inspiratory circuit, on which an inspiratory flow sensor is installed, wherein the inspiratory flow sensor is calibrated according to temperature, pressure and humidity in the inspiratory circuit, and a gas constant of the gas;
   a proximal circuit, through which a patient inhales and exhales, on which a proximal flow sensor is installed, wherein the proximal flow sensor is calibrated according to temperature, pressure, and humidity in the proximal circuit, and a gas constant of the gas; and
   an expiratory circuit, on which an expiratory flow sensor is installed, wherein the expiratory flow sensor is calibrated according to temperature, pressure and humidity in the expiratory circuit, and a gas constant of the gas.

3. The ventilating system according to claim 2, wherein a flow control valve is installed at the inspiratory circuit to adjust the flow rate according to reading of the inspiratory flow sensor.

4. The ventilating system according to claim 2, wherein the inspiratory flow sensor, the proximal flow sensor and the expiratory flow sensor are calibrated further according to viscosity when the flow rate drops under a certain magnitude.

5. The ventilating system according to claim 2, wherein inspiratory flow sensor, the proximal flow sensor and the expiratory flow sensor are calibrated based on a reference volumetric flow calculated at a body temperature, a gas constant of air, and a barometric pressure.

6. The ventilating system according to claim 5, wherein the reference volumetric flow is pre-stored in a calibration table.

7. The ventilating system according to claim 6, wherein the reference volumetric flow is converted from a volumetric flow calculated at 21% of oxygen, ambient pressure and temperature.

* * * * *